United States Patent [19]
Paradis

[11] Patent Number: 5,688,253
[45] Date of Patent: Nov. 18, 1997

[54] NEEDLE LOCKING SYSTEM

[76] Inventor: Joseph R. Paradis, P.O. Box 22238, Hltn Hd Is., S.C. 29925

[21] Appl. No.: 456,051

[22] Filed: May 31, 1995

[51] Int. Cl.$^6$ ................................................ A61M 5/00
[52] U.S. Cl. ......................... 604/263; 604/164; 604/198
[58] Field of Search ............................ 604/263, 198, 604/192, 158–164, 168, 171, 165, 280, 283, 195

[56] References Cited

U.S. PATENT DOCUMENTS

| | | | |
|---|---|---|---|
| 5,215,528 | 6/1993 | Purdy et al. | 604/164 |
| 5,248,301 | 9/1993 | Koenig, Jr. et al. | 604/164 |
| 5,279,590 | 1/1994 | Sinko et al. | 604/162 X |
| 5,322,513 | 6/1994 | Walker | 604/161 |
| 5,376,075 | 12/1994 | Haughton et al. | 604/171 X |
| 5,376,082 | 12/1994 | Phelps | 604/158 X |

*Primary Examiner*—John D. Yasko
*Attorney, Agent, or Firm*—George E. Kersey, Esq.

[57] ABSTRACT

An assembly of a needle, catheter, and a device for selectively protecting the needle tip from inadvertent needle sticks by an elongate housing having an extending needle and a needle guard adapted for sliding movement relative the housing. The needle guard is formed to carry a catheter hub and catheter, and includes an actuation tab to enable selective sliding movement of the needle guard relative the housing and along the length of the needle. The housing is adapted to be held within one hand to permit insertion of the needle and catheter into a patient, and after insertion, the needle may be withdrawn from the patient and covered by the needle guard by pressing against the actuation tab while slidably retracting the housing and needle relative to the needle guard; upon full retraction of the housing, a detent mechanism formed between the housing and needle guard locks the needle guard about the length of the needle and prevents accidental contact with the needle tip.

19 Claims, 8 Drawing Sheets

NEEDLE LOCKING SYSTEM

This invention relates to procedures requiring the use of needless and more particularly, to the safe use needles in such procedures.

BACKGROUND OF THE INVENTION

In many cases which require the use or needles, such as medical procedures in which fluids are applied or withdrawn, special precautions must be taken to avoid accidental "needle sticks" which could place users at serious risk. Once the needles have served their purposes, and are "spent", they generally are broken to prevent reuse and discarded in special waste containers.

Despite the taking of special precautions, there is always the possibility of accidental needle contact and attendant injury, exposing user personnel to substantial risks.

Such risks have become acute with medical and biological procedures because of the danger from fluid borne pathogens, such as viruses of the HID (Human Immune Deficiency) type which are believed to cause AIDS (Acquired Immune Deficiency Syndrome), and the viruses associated with Hepatitis.

Because of the safety hazards associated with inadvertent needle sticks, a number of devices have been introduced. One such device is the "HR" Needle of ICU Medical, Inc, of Laguna Hills, Calif. The HR device almost completely encloses a needle subsequent to use, but it does not provide a protective cover for the needle tip. This presents the possibility of an accidental stick or scratch. In addition, for the HR needle and other prior needles, it is difficult to apply a safety cover over a spent needle. As a result, during manipulation, there is always the possibility of a slip that could result in an inadvertent needle stick.

In U.S. Pat. No. 4,327,723 of May 4, 1982, Paul L. Frankhouser discloses a shield assembly for a catheter, particularly for protecting flow directed catheters used in measuring central venous pressure and pulmonary wedge pressure. The shield assembly includes front and rear hubs sized to permit through movement of the catheter and a feed tube for interconnecting the front and rear hubs. The sheath is substantially longer than the feed tube and is collapsible to permit feed tube interconnection of the hubs, and is extendible to shield a substantial length of catheter.

In U.S. Pat. No. 4,559,043 of Dec. 17, 1985, Whitehouse et al. disclose an assembly for connecting needles and catheters used in intravenous applications and chemical analysis. A leak-proof, sterile and self-sealing septum is provided for needle insertion. When the needle is retracted from the septum, it reseals and maintains leakproof sterility. The distal end of the assembly has an outlet bore through which a catheter is inserted, and the proximal end of the assembly is connected to an external adaptor to which a needle is attached. The septum is positioned between the distal end and the proximal end to provide self-sealing between the needle and the catheter.

In U.S. Pat. Nos. 4,762,516 of Aug. 9, 1988 and 4,832,696 of May 23, 1989, Luther et al. disclose an assembly for protecting a needle tip. The assembly includes an elongate housing which mounts the needle, and a needle guard is slidably mounted within the housing and adapted to be moved forwardly along the needle. Following use, the needle and housing are retracted and the needle guard permanently locks with the housing while occluding or covering the needle.

In U.S. Pat. No. 4,950,252 of Aug. 21, 1990, Luther et al. disclose an assembly of a needle, catheter, and a device for selectively protecting the needle tip against inadvertent needle sticks. An elongate housing has an extending needle, and a needle guard adapted for sliding movement relative to the housing. The needle guard carries a catheter hub and catheter, and includes an actuation tab to enable selective sliding movement of the needle guard relative to the housing and along the length of the needle. The housing is adapted to be held within one hand to permit insertion of the needle and catheter into a patient, and after insertion, the needle may be withdrawn from the patient and covered by the needle guard by pressing against the actuation tab with the index finger, while slidably retracting the housing and needle relative to the needle guard by use of the thumb and middle finger. Upon full retraction of the housing relative to the needle guard, a detent formed between the housing and needle guard is engaged to permanently lock the needle guard about the length of the needle and prevent accidentally contact with the tip.

In U.S. Pat. No. 4,964,854 of Oct. 23, 1990, Luther discloses an "over-the-needle" catheter assembly which incorporates a shield that is operative to prevent inadvertent needle trauma after the needle has been withdrawn from a surrounding catheter sheath. A tubular catheter sheath has an elongated needle initially disposed in an "assembled" position within the lumen of the tubular sheath, and is subsequently withdrawable to a "retracted" position outside the lumen of the tubular sheath. A shield is incorporated into the catheter assembly and is operative to shield and attach to the tip of the needle when it is withdrawn from its initial "assembled" position within the tubular sheath.

In U.S. Pat. No. 5,120,317 of Jun. 9, 1992, Luther discloses a vascular/venous access device with a catheter and needle having corresponding stops at their distal ends. The needle within the catheter is disposed so that the catheter and needle stops abut to prevent the catheter from traveling axially upward during insertion. The catheter stop may soften when exposed to blood so that while generally rigid during insertion, it becomes more flexible after the catheter resides in a vein. The needle may be disposed within the catheter with the sharp end extending outwardly beyond the distal end of the catheter. A telescoping assembly may be used.

In U.S. Pat. No. 4,383,857 of Jan. 24, 1995, Levitov discloses a moveable guard sheath that is released and moved over the length of a syringe barrel to prevent contact with the syringe needle.

In U.S. Pat. No. 5,383,863 of Jan. 24, 1995, Mardones discloses an attachment for standardized hypodermic syringes with a protector tube that slides over the syringe and is secured by a catch spring with a split ring that constricts onto the hub of the syringe needle and has resilient legs that engage a longitudinal slot in the protector tube. A detent at an outer end of the slot is for retracted positioning of the protector tube exposing the needle, and a lock is provided at an inner end of the slot for permanent extended positioning of the protector tube covering the needle.

In U.S. Pat. No. 5,385,555 of Jan. 31, 1995, Hausser discloses a lockable safety shield for a hypodermic syringe. The safety shield is mounted over the syringe barrel and can be telescoped into a position for protectively guarding a sharp point on the needle cannula. Oppositely facing stop surfaces on the syringe barrel and the safety shield prevent complete telescoped removal of the safety shield from the syringe barrel. A deflectable wall on the syringe barrel snaps into engagement with locking teeth on the safety shield when the safety shield has been telescoped into a position for guarding the needle cannula point to prevent exposure of the used needle cannula.

In U.S. Pat. No. 5,385,556 of Jan. 31, 1995, Wang et al. disclose an endcap for a hypodermic syringe. The endcap has a sheath and a base section. The sheath, having proximal and distal ends, is hollow and resiliently deformable with a slit extending substantially the length of the sheath. The proximal end of the sheath is open. The base section is attached to and extends radially outwardly from the periphery of the sheath's proximal end. The base section is disposed opposite the slit and includes two spaced apart, outwardly extending leg supports.

In U.S. Pat. No. 5,385,557 of Jan. 31, 1995, Thompson discloses a retractable needle shielding device for use with a medical syringe devised to reduce the risk of inadvertent needle strikes. The shield includes a retractable tubular body movable from a position completely shielding the needle to a position where the needle extends outward from the tubular body. The tubular body may be configured to retract over the barrel of the syringe and, which, in such case, should be formed of a substantially transparent material. The shield may include a collar engageable in series with, and in fluid communication with the nose of the barrel and the hub of the needle. The collar preferably includes radially extending guides which are engageable with grooves disposed interiorly of the tubular body. The collar may be substantially the same length as the tubular body and, therefore, not retract over the syringe barrel. Frictional elements are provided to resist the displacement of the tubular body relative to the syringe. The tubular body is dimensioned and configured to be extensible over the length of a syringe needle and the needle cap.

The foregoing all provide complex devices and techniques for avoiding needle sticks. Accordingly it is a principal object of the invention to simplify devices and methods for avoiding needle sticks. A related object of the invention is to overcome the disadvantages and difficulties presented by the prior art.

SUMMARY OF THE INVENTION

In accomplishing the foregoing and related objects, the invention provides a catheter assembly formed by a needle housing with a needle mounted thereon and extending therefrom. A needle guard is slidably mounted on the housing, and a hub with a catheter mountable therein is engageable with the needle guard and needle. As a result, the needle guard can cover the needle before insertion into a patient, is retracted and slidably disengaged from the hub to permit insertion of the needle and the catheter into a patient and thereafter receives and guards the needle during its withdrawal from the patient, allowing the catheter to remain in the patient.

In accordance with one aspect of the invention a detent locking lever on the needle housing engages the needle guard for holding it in a retraction or reception position with respect to the needle. The needle guard can include a plurality of detent recesses which are engageable by the locking lever for holding the guard in a retraction or reception position with respect to the needle.

In accordance with another aspect of the invention, the needle guard has a slot that extends from a distal to a proximal end of the guard and is engageable with the hub along the slot, which can have a non-uniform width to accommodate the hub when the guard is in position to cover the needle. The hub can include an extension above the engagement of the hub with the needle guard.

The hub also can include a channel for the catheter and the extension can receive a tube that communicates with the channel to permit fluid to be injected or withdrawn through the tube. The tube can have an input port connected to a Luer fitting, and the Luer fitting can include a flow-control valve that is connectable to a hydrophobic filter cap.

In accordance with a further aspect of the invention, the needle housing includes a channel extending within the housing from the distal end of the needle to permit fluid flashback when the needle is inserted into a patient in order to indicate that a successful entry of the catheter has been made into the patient.

In a method of affixing a catheter to a patient, the steps include grasping a catheter assembly having a hub with a needle and catheter therein protected by a slidably-mounted needle guard on a housing for the needle; retracting the needle guard to expose the hub and combination of needle and catheter which are inserted into a patient; retracting the needle into the needle guard to withdraw it from the catheter and disengaging the needle guard from contact with the hub, with the needle completely shielded by the needle guard.

In accordance with one aspect of the method, the retraction of the needle guard is by sliding the needle guard with respect to the hub to expose the needle and simultaneously disengage the needle guard from sliding contact with the hub. The method also includes sliding the needle guard until a locking detent mechanism of the housing is engaged. The retraction of the needle is by extending the needle into the needle guard until the needle and needle guard are completely disengaged from the hub.

In a method of inserting a catheter into a patient, the steps include retracting a needle guard slidably mounted over a housing having a needle extending therefrom, with a catheter disposed along the length of the needle; inserting the needle and catheter into a patient and thereafter removing the needle from the catheter while maintaining the catheter in the patient by manually retracting the needle into the needle guard; and disengaging the needle guard from the catheter with the needle enclosed in the guard to permit unit removal of the housing, needle guard and needle, while the catheter remains in the patient.

A percutaneously insertable over-the-needle catheter assembly of the invention includes a tubular catheter having a proximal end, a distal end, and an axially-extending tubular lumen. A needle with a proximal end and a sharpened distal end is axially disposed within the lumen of the tubular catheter so that the sharpened distal end of the needle extends beyond the distal end of the tubular catheter. The needle guard has an interior needle-receiving passage and is axially retractable from a first needle position, where the sharpened distal tip of the needle is shielded by the needle guard, to a second needle position where the needle is exposed for insertion into a patient. A plunger is attached to the needle for manually returning the needle to the first needle position where the sharpened distal end of the needle is shielded by the needle guard and the needle and needle guard are disengaged from the catheter.

The catheter assembly can further include a finger engagement tab attached to and extending outwardly from the plunger. A channel in the plunger is in communication with the proximal end of the needle for providing controlled blood flashback in order to indicate that the catheter has been properly inserted into the patient. The catheter plunger and needle guard can further have first and second detent lock portions formed on the needle guard, positioned and configured to engage a locking lever of the plunger when the needle reaches the first or second needle locking position.

DESCRIPTION OF THE DRAWINGS

Other aspects of the invention, as well as other features, will become apparent after considering several illustrative embodiments, taken with reference to the drawings in which:

FIG. 8B is top view of the complete unit shown in cross-section in FIG. 8A showing the nature of the contact of the neck with the needle guard;

DETAILED DESCRIPTION OF PREFERRED EMBODIMENTS

Figures 1A, 1B:
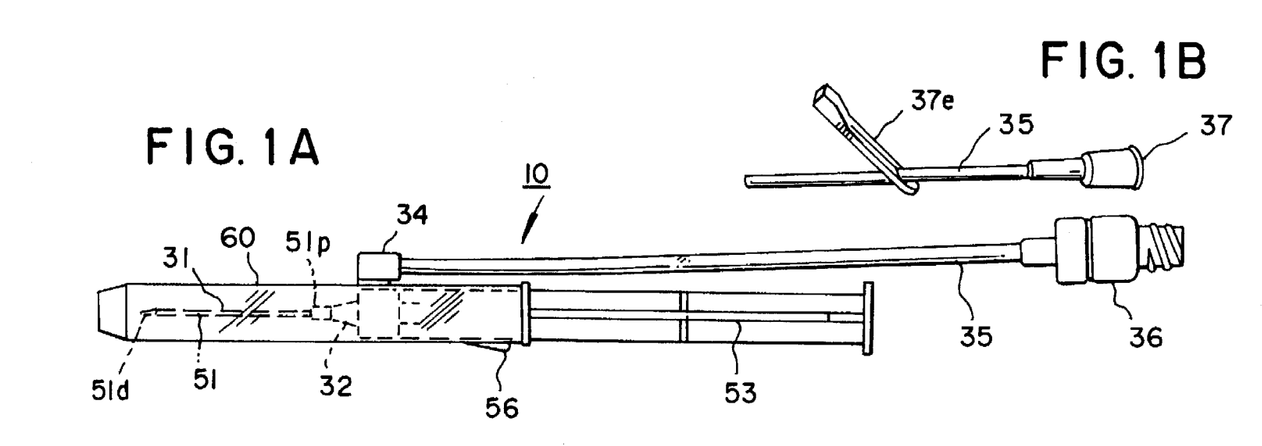
FIG. 1A is a full-scale view of the needle-protected catheter assembly of the invention showing a needle guard locked in position for needle protection.
FIG. 1B is a full-scale view of an alternate tube fitting for the needle-protected catheter assembly of FIG. 1A showing a needle guard locked in position for needle protection.

With reference to the drawings, FIG. 1A shows a full-scale view of the needle-protected catheter assembly 10 of the invention with a needle guard 60 locked for protection with respect to a needle 51 having a sharpened or beveled distal end 51d and an opposing proximal end 51p. The needle 51 is within a catheter 31 that projects from a catheter hub 32. Extending from the catheter hub 32 by a neck 33 that is an extension 34 which receives a micro-tube 35 having its receiving end connected to a valve 36.

Figure 5A:
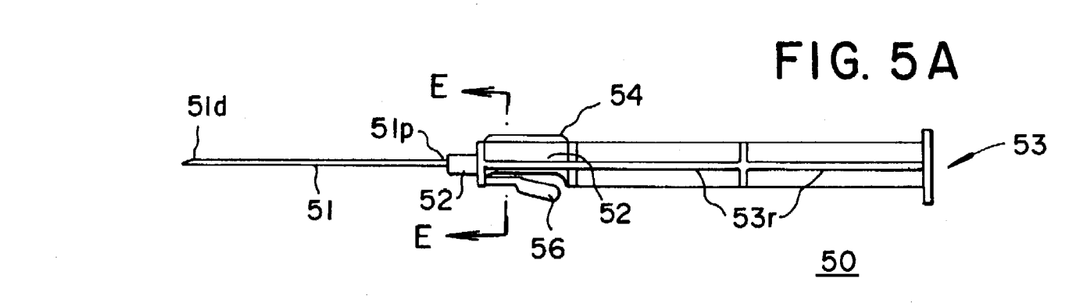
FIG. 5A is plan view of a needle stylet assembly in accordance with the invention, including a mount for the needle and a plunger for moving the mount.

The needle 51 is part of a needle styler assembly 50, shown in detail in FIG. 5A, and is attached to a mount 52 that terminates in a hand-operable plunger 53.

All parts, except for the needle 51, preferably are formed of plastic, such as medical grade injection molded polycarbonate or polystyrene.

Figure 5B:
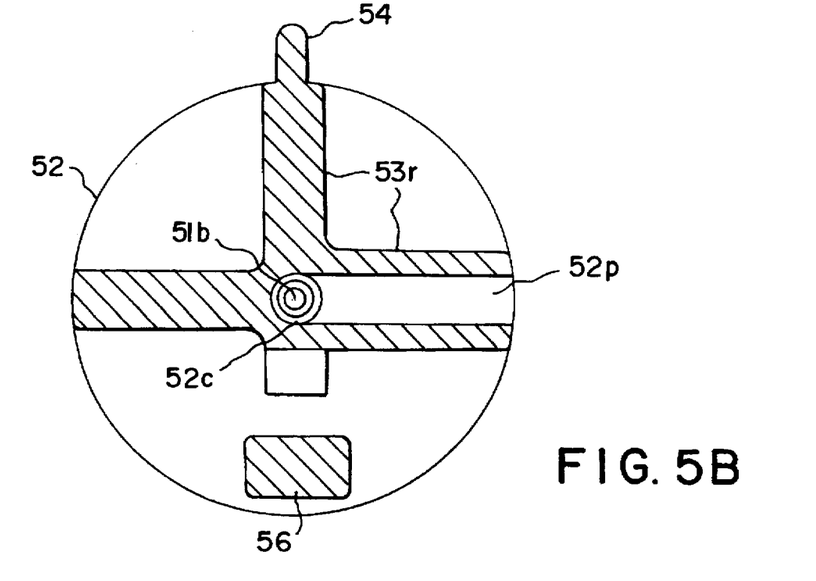
FIG. 5B is cross-sectional view taken about lines E—E of FIG. 5A showing an auxiliary channel communicating with the bore of the needle to permit fluid flashback for indicating when the needle has been successfully inserted.

The mount 52, as shown in FIGS. 5B and 8B, has an interior channel 52c that communicates with the bore 51b of the needle 51, which is rigidly retained by the mount 52. The end of the needle 51 terminates in a bevelled tip 51t. The interior of the channel 52c formed within the mount 52 has a passageway 52p, as described in detail below, for controlled blood flashback to give the user an indication that a proper insertion has been made of the catheter 31. The mount 52 extends to the plunger 53 that preferably is provided with cross ridges 53r and a cylindrical end 53c adapted to be grasped by the hand of a user.

Figures 1C, 1D:
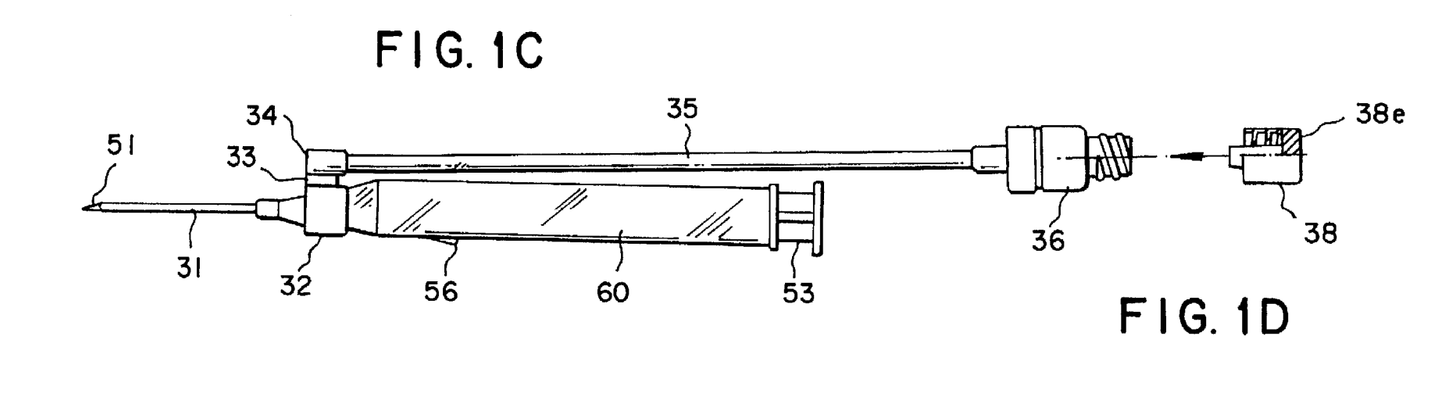
FIG. 1C is a full-scale view of the needle-protected catheter assembly of the invention showing the needle guard of FIG. 1A retracted for patient insertion.
FIG. 1D is a full-scale view of a hydrophobic filter cap for the needle-protected catheter assembly of FIG. 1C.
Figure 6A:
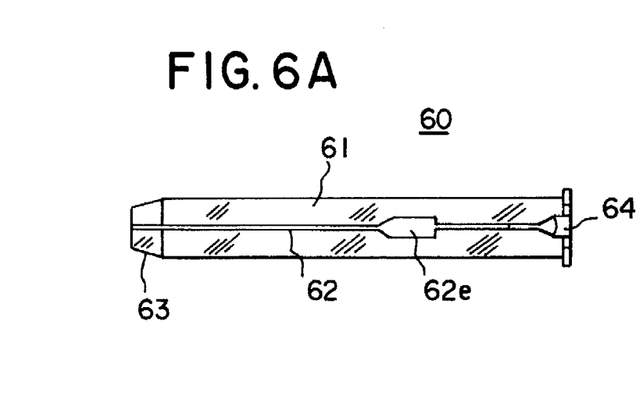
FIG. 6A is a top view of the needle guard of the invention that is slidably movable with respect to the neck of the catheter hub of FIGS. 4A–4D and over the stylet of FIG. 5A.

The needle guard 60, detailed in FIGS. 6A–6D, preferably is formed as an elongated tubular member 61 having an axial wall slot 62 extending substantially throughout the length of its upper surface shown in FIG. 6A. The slot 62 engages the neck 33 of the catheter hub 32. When the guard 60 is positioned as shown in FIG. 1, an enlargement 62e of the slot 62 surrounds the neck 33. The needle guard 60 preferably is fabricated to envelope the needle 51, and its associated hub 32, such that the needle guard 60 may be slidably moved over the mount 52. During sliding movement from the enlargement 62e the guard 60 expands and opens the slot 62 to the width of the enlargement 62. When such movement takes place, the needle guard 60 adopts the position shown in FIG. 1C, exposing the catheter 31 and the needle 51 for insertion into a patient.

Figure 2A:
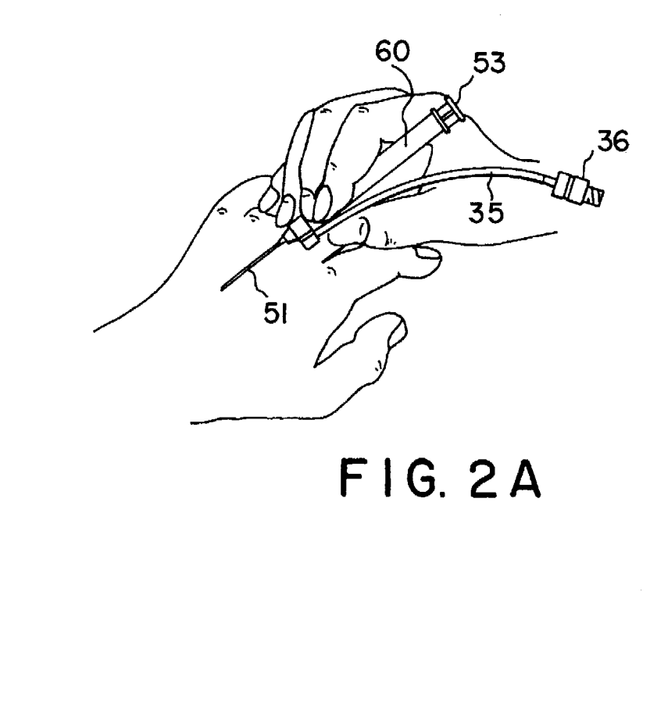
FIG. 2A is a perspective view showing the needle guard of FIG. 1C retracted, with the needle tip and catheter ready for insertion into a fluid passage in the hand of a patient.
Figure 2B:
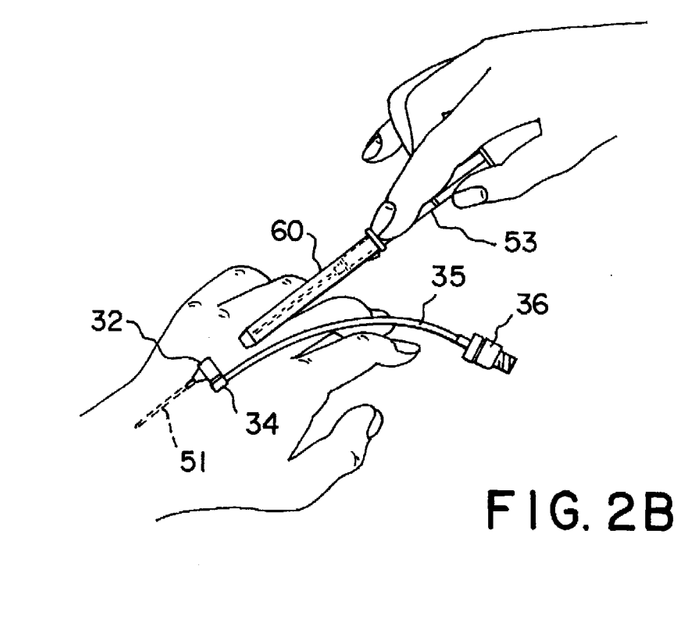
FIG. 2B is a perspective view showing needle tip and catheter of FIG. 1C inserted into the hand of a patient, with the needle and guard being removed as a unit after controlled blood flashback is observed and the needle guard has been moved forwardly to retract the needle into the guard and simultaneously disengage it from the catheter.

As shown in FIG. 2A, the assembly 10 is gripped, e.g. by the hand H of a medical operative and brought to the appropriate location on a patient, such as the hand H' where a venipucture or arterial puncture can take place as illustrated in FIG. 2B.

The invention provides controlled fluid, e.g. blood, flashback to indicate successful completion of a needle puncture. In prior art devices, the fluid pressure at a puncture site can be so great that blood can forcibly squirt from the site and cause undesirable contamination which is prevented by the invention.

Figure 6B:
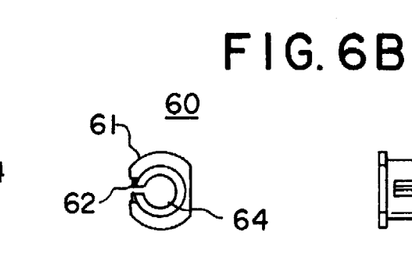
FIG. 6B is a end view of the needle guard of FIG. 6A showing the proximal end of the channel that contacts the neck joining the hub to the extension in FIG. 4A.
Figure 6C:
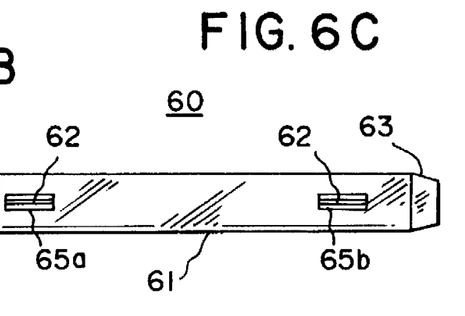
FIG. 6C is a bottom view of the needle guard of FIG. 6A showing detent positions for locking engagement with the lever of the stylet shown in FIG. 5A.
Figure 6D:
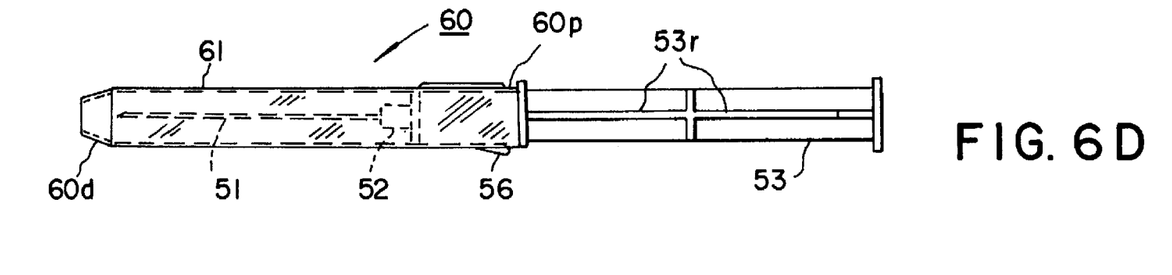
FIG. 6D is a side view showing the needle guard of the invention locked over a needle and ready for proper disposal.

The needle 51 and guard 60 are ready for removal after needle and catheter insertion showing the controlled blood flow of the invention. This can be accomplished as shown in FIG. 2B by having the index finger I of the hand H positioned against the guard 60 to permit single-handed withdrawal of the plunger 53 by thumb pressure against the plunger as shown. At the conclusion of the withdrawal, the needle guard 60 is locked over the needle 51 as shown in FIG. 6D. The catheter assembly 30, including the extension 34 to the inlet valve remain as shown in FIG. 2C.

The distal end 60d of the needle guard 60 is provided with a tapered end 63, while the proximal end 60p has a guide opening 64 that engages a guide rib 54 of the stylet assembly 50. An actuation tab 56 extends outwardly from one surface of the stylet 50 to an elevation beyond the outer surface of the guard 60. Near opposite ends of the needle guard 60 are locking apertures 65 and 66 which are formed in a complimentary configuration to the locking tab or lever 56.

It will be recognized, that the outward biasing of the tab 56, and expansion of the guard 60 widening the slot 62 is primarily the result of using plastics such as polystyrene and polycarbonate which have flexible memory.

Figure 2C:
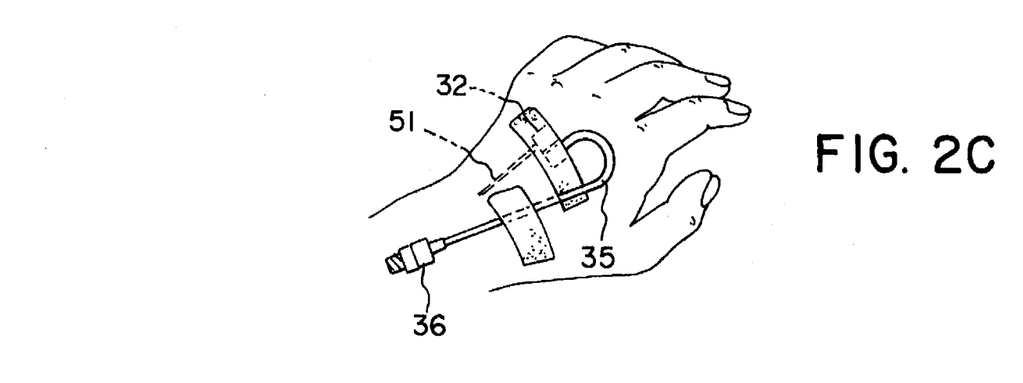
FIG. 2C is a perspective view showing the catheter of FIG. 1C in the patient, who is ready for repeated infusions or aspirations, without any further use of needles, through a micro-tube connected to needleless-operable control valve as shown in FIG. 1C.

Upon relative sliding movement of the needle guard 60 relative to the needle stylet 50, the needle guard 60 will travel from its relative orientation depicted in FIG. 2A, to an intermediate orientation shown in FIG. 2C, and then to a final orientation depicted in FIG. 6D. As a preliminary to such sliding movement, the locking tab 56 has entered the locking detent aperture 66 of the guard 60, then enters the forward locking detent aperture 65, finally returning to the initial locking detent aperture 66.

It will be recognized that discard of the locked needle-guarded needle in FIG. 6D may be made without fear of any inadvertent needle stick. The guard 60 extends completely about and encloses the needle 51, with the position of the needle guard 60 relative the housing being maintained by the lock detent mechanism.

Subsequently, a conventional fluid line (not shown) may be attached to the valve 36 of the micro-tube 35 which extends to the catheter 31 remaining with the patient.

While the microtube 35 of FIG. 1A extends to a valve 36 of the kind disclosed in my co-pending patent application Ser. No. 08/135,673 filed Oct. 13, 1993, the valves in my subsequently filed co-pending applications may be employed as well. In addition, in place of the valve 36, the alternate tube fitting of FIG. 1B may be employed where the microtube 35 extends to an ordinary Luer fitting 37 and the effect of my valve 36 is attempted by a clamp 37c which is secured to the microtube 35 in the vicinity of fitting 37.

In FIG. 1D a hydrophobic filter cap 38 is used for the needle-protected catheter assembly of FIG. 1C, which is a full-scale view of the needle-protected catheter assembly of the invention showing the needle guard of FIG. 1A retracted for patient insertion. The hydrophobic filter cap 38 is threaded on the valve 36 and includes a filter element 38e which prevents the passage of fluid and allows only the passage of air.

Figure 3:
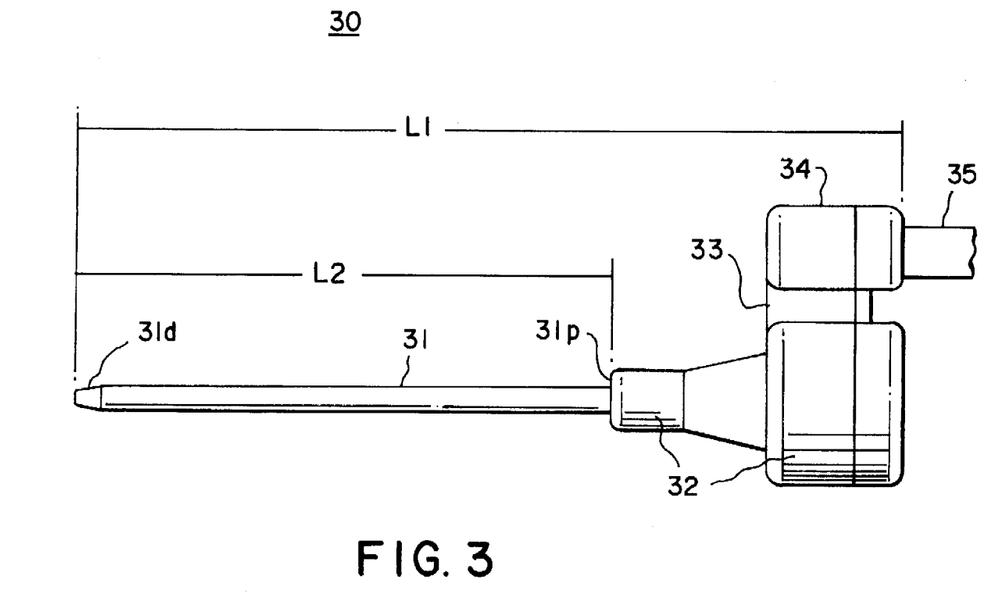
FIG. 3 is a side view of the catheter inserted in FIGS. 2B and 2C, together with its mounting hub and extension which receives a micro-tube through which infusion or aspiration of fluids can take place.

The catheter unit 30 detailed in side view in FIG. 3 has a conventional catheter tube 31 with a proximal end 31p inserted into the catheter hub 32 while the distal end 31d is tapered to fit appropriately over the needle 51 (not shown). The catheter has a length L2 that extends from the proximal end 31p to the distal end 31d. The hub 32 extends by the neck 33 to the extension 34 where the microtube 35 (shown partially) is attached through which infusion or aspiration of fluids can take place. The length from the position of insertion of the microtube 35 to the distal end 31d of the catheter 31 is given by L1.

Figure 4A:
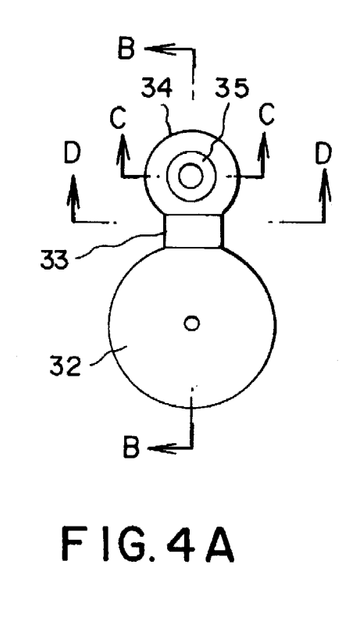
FIG. 4A is an end view of FIG. 3 showing the mounting hub joined by a neck to the extension which receives the micro-tube of FIG. 1C.

In FIG. 4A the catheter unit 30 is shown in an end view of FIG. 3, with the mounting hub 32 joined by the neck 33 to the extension 34 which receives the microtube 35 of FIG. 1C. The section lines B—B, C—C and D—D are for sectional views shown in respective FIGS. 4B, 4C and 4D.

Figure 4B:
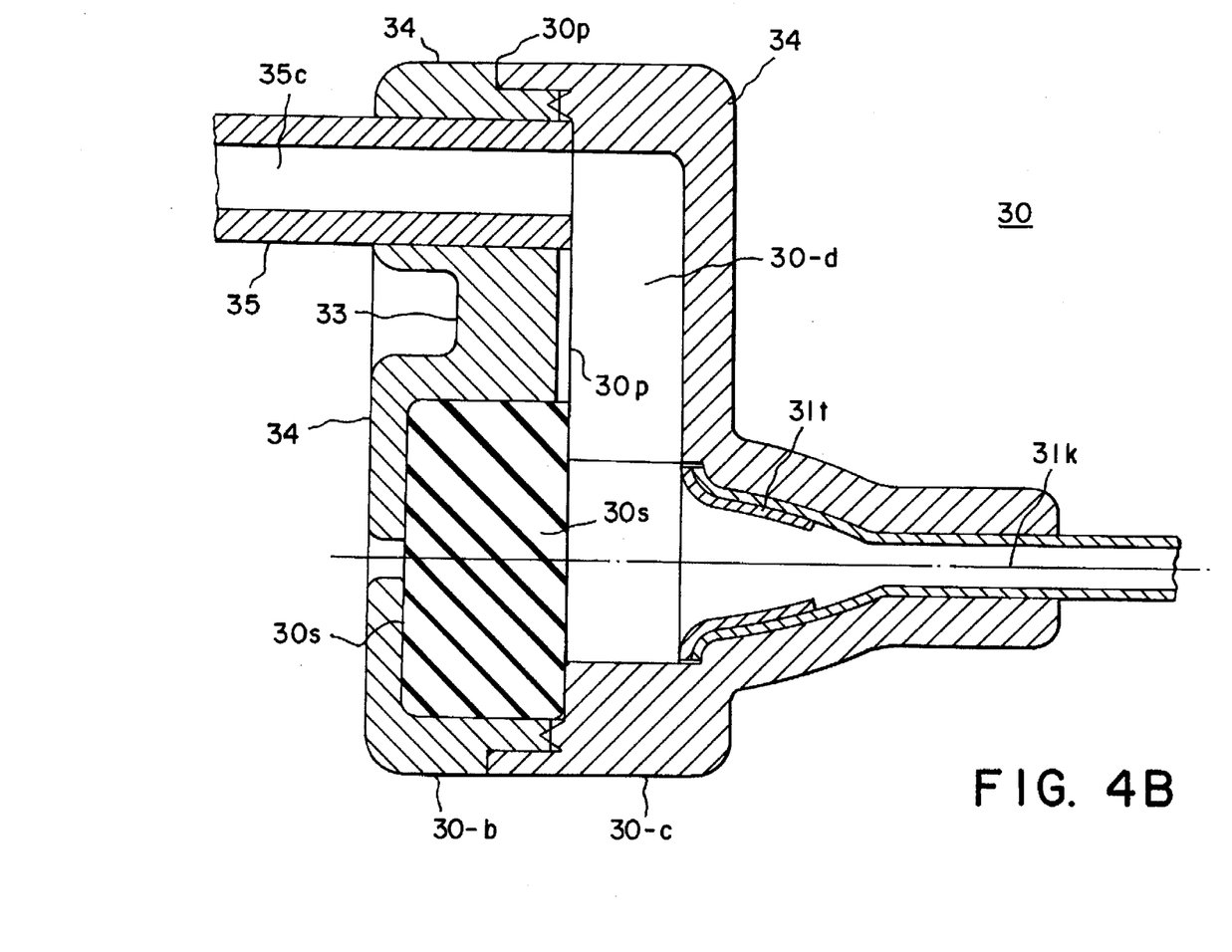
FIG. 4B is an enlarged cross-sectional view taken about lines B—B of FIG. 4A showing the internal structure of the hub, neck and extension formed by joining a cap to a base.

With reference to FIG. 4B, the enlarged cross-sectional view taken about lines B—B of FIG. 4A shows the internal structure of the hub 32, the neck 33 and the extension 34 formed by joining a cap 30-c to a base 30-b, which include respective halves of the overall catheter unit and are joined together, illustratively by ultrasonic welding at a parting line 30p between the two halves. The microtube 35 is inserted into the extension 34 to an orthogonally disposed channel 30-d that extends from the microtube channel 35c to the catheter channel 31k. The catheter 31 is held in position within the hub 32 by a conventional insert 31t. The catheter unit 30 includes a seal plug 30-s that is in the base portion of the hub 30. This plug 30-s serves the important function of sealing the needle withdrawal passage after the catheter sleeve 31 has been inserted into a patient.

Figures 4C, 4D:
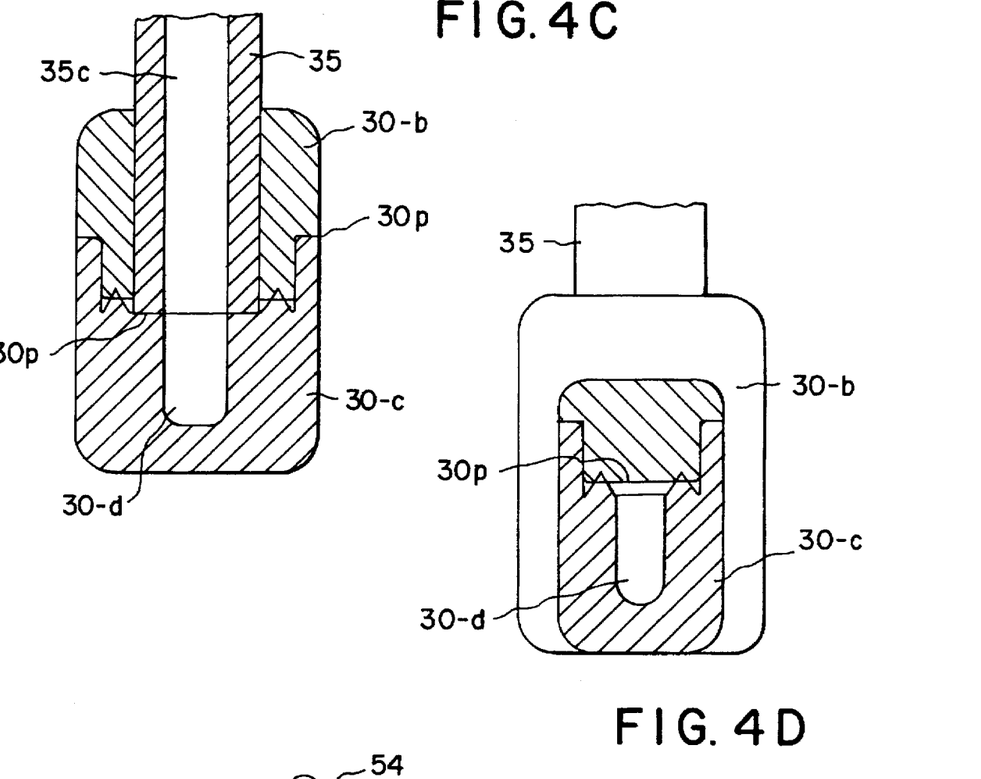
FIG. 4C is cross-sectional view taken about lines C—C of FIG. 4A showing the interlock of the base and cap forming the neck and extension from the hub.
FIG. 4D is cross-sectional view taken about lines D—D of FIG. 4A showing further features of the interlock of FIG. 4C.

In the cross-sectional view of FIG. 4C, taken about lines C—C of FIG. 4A, the interlock of the base 30-b and the cap 30-c is shown forming the neck 33 and extension 34 from the hub 32.

In the further cross-sectional view of FIG. 4D, taken about the lines D—D of FIG. 4A, further features are shown of the interlock of FIG. 4C taken across the extension 33.

In the plan view of the needle stylet assembly 50 of FIG. 5A, a mount 52 includes an actuation tab 56 and extends to a plunger 53. The front of the mount includes the needle 51 and the actuation tab 56 secures the needle stylet assembly in its needle-protected position until the catheter assembly 10 is to be used.

The stylet assembly 50 of FIG. 5A includes, as shown in the cross-sectional view taken about lines E—E of FIG. 5A, an auxiliary channel 52c that communicates with the bore 51b of the needle 51 to permit fluid flashback for indicating when the needle 51 has been successfully inserted.

Details of the needle guard 60 of the invention that is slidably movable with respect to the neck 33 of the catheter hub 32 of FIGS. 4A–4D, and over the stylet 50 of FIG. 5A, are shown in the top view of FIG. 6A. A end view of the needle guard 60 of FIG. 6A is shown in FIG. 6B. FIG. 6C shows a bottom view of the needle guard 60 of FIG. 6A with detent positions 65a and 65b for locking engagement with the lever 56 of the stylet 50 shown in FIG. 5A. FIG. 6D is a side view showing the needle guard 60 locked over a needle 51 and ready for proper disposal.

Figure 7:
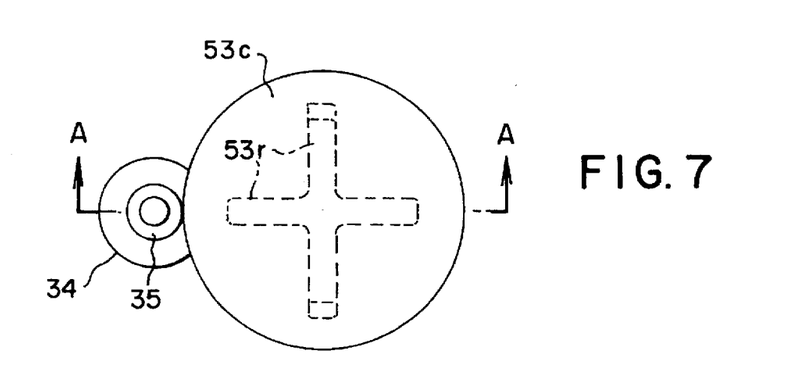
FIG. 7 is a partial end view of the needle-protected catheter assembly of the invention taken from the plunger side and showing the relationship of the plunger to the extension from the catheter hub.

FIG. 7 is a partial end view of the needle-protected catheter unit 30 of the invention taken from the side of the plunger 53 showing the relationship of the plunger 53 to the extension 34 from the catheter hub 32.

Figure 8A:
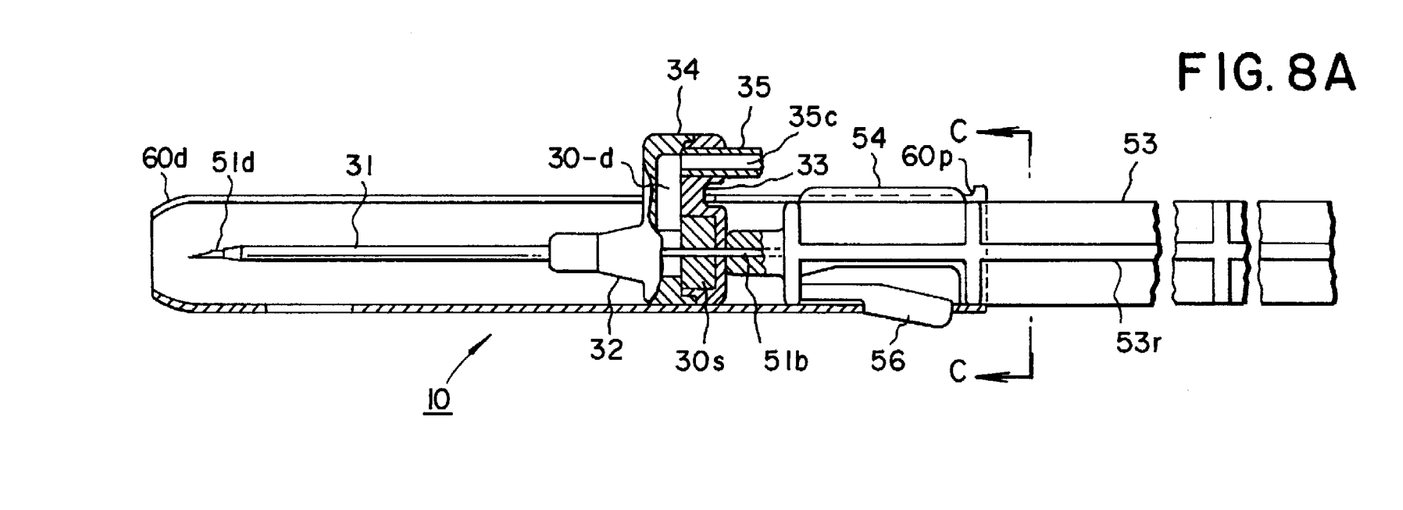
FIG. 8A is a partial cross-sectional view taken about lines A—A of FIG. 7 showing engagement of the stylet lever with the needle guard in its forward guard position.

In the partial cross-sectional view of FIG. 8A, taken about lines A—A of FIG. 7, the engagement of the stylet lever 56 is shown with the needle guard 60 in its forward guard position. A top view of the complete cross-sectional unit in FIG. 8A is shown in FIG. 8B, illustrating the nature of the contact of the neck 33 with the needle guard 60.

Figure 8C:
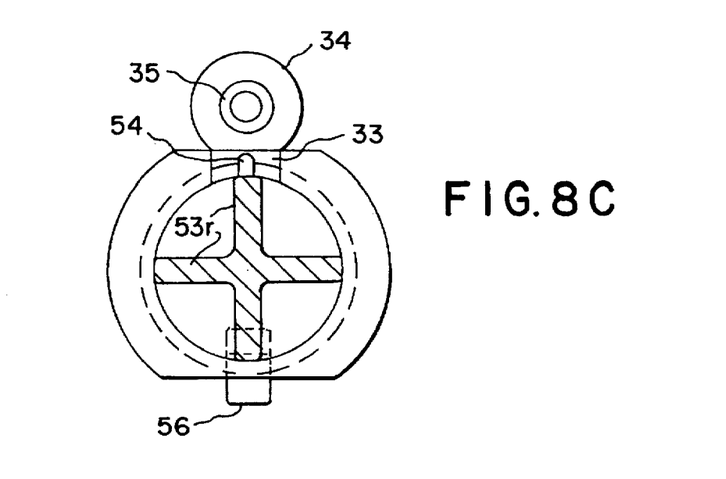
FIG. 8C is cross-sectional view taken about lines C—C of FIG. 8A showing the relationship of the plunger to the catheter hub, neck and extension.
Figure 8D:
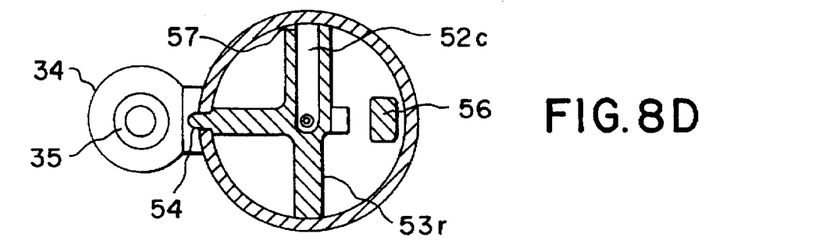
FIG. 8D is cross-sectional view taken about lines D—D of FIG. 8B showing the auxiliary channel in the needle mount for controlled blood flashback.
Figure 8E:
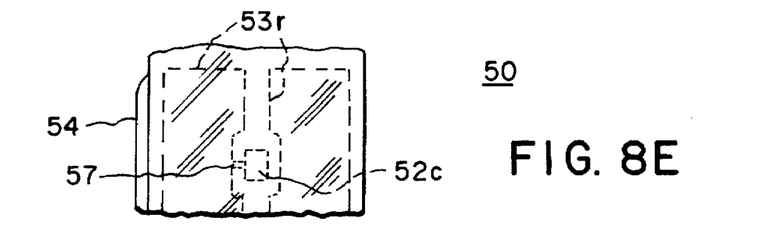
FIG. 8E is a partial view of the top of the needle-guarded plunger of FIG. 8D showing the air-vent construction of the invention associated with observing controlled blood flashback.

Details of the relationship of the plunger 53 to the catheter hub 32, the neck 33 and the extension 34 are included in FIG. 8C, which is cross-sectional view taken about lines C—C of FIG 8A. In the cross-sectional view of FIG. 8D, taken about lines D—D of FIG. 8B, the auxiliary channel 52c is shown in the needle mount 52 for controlled blood flashback. In the partial view of the top of the needle-guarded plunger 53 of FIG. 8D, the air-vent construction of the invention associated with observing controlled blood flashback is shown.

From the above, it will be recognized that the present invention constitutes a significant improvement in the art. It allows insertion of a catheter into a patient and subsequent withdrawal of an associated needle, which can be accomplished by use of a single hand and simple hand manipulation, while allowing the catheter to remain properly positioned in the patient. Additionally, it will be recognized that the withdrawal of the needle 51 from the patient may be effectuated without ever exposing the needle to the medical user, since the needle guard 60 may be maintained in engagement with the catheter unit 30 and not disengaged until such time as disposition is to be made of the entire needle 51 within the interior of the guard 60.

It further will be recognized that from the construction and method of utilizing the invention, a user may withdraw and subsequently lock the needle within the interior of the needle guard with a single hand and in a simple manipulative fashion.

Although certain materials, configurations and procedure have been disclosed, those skilled in the art will recognize that various modifications and adaptations can be made without departing from the spirit and scope of the invention, and any such modification and adaptations are contemplated as being included in the invention.

What is claimed is:

1. A catheter assembly comprising:
    a needle mount with a needle thereon and extending therefrom;
    a hub with a catheter surrounding said needle;
    a needle guard slidably disposable over said needle mount and engageable with said needle mount to cover said needle before insertion into a patient, and is retractable and slidably disengageable from said hub to expose said needle and permit insertion of said needle and said catheter into said patient, and thereafter is separable from said hub while receiving and guarding said needle during its withdrawal from said patient, completely covering said needle after withdrawal while allowing said catheter to remain inserted.

2. The assembly claim 1 further comprising a detent locking lever on said needle housing for engaging said needle guard for holding it in a retraction or reception position with respect to said needle.

3. The assembly of claim 1 wherein said needle housing includes a channel extending within said housing from the distal end of said needle to permit fluid flashback when said needle is inserted into said patient;
    thereby to indicate that a successful entry has been made for said catheter into said patient.

4. A catheter assembly comprising:
    a needle mount with a needle thereon and extending therefrom;
    a needle guard slidably disposable over said mount;
    a hub with a catheter positionable therein and surrounding said needle, with said hub engageable by said needle guard;
    whereby said needle guard covers said needle before insertion into a patient, is retractable and slidably disengageable from said hub to expose said needle and permit insertion of said needle and said catheter into said patient and thereafter is separable from said hub while receiving and guarding said needle during its withdrawal from said patient, allowing said catheter to remain inserted;
    further comprising a detent locking lever on said needle housing for engaging said needle guard for holding it in a retraction or reception position with respect to said needle, and said needle guard includes a plurality of detent recesses which are engageable by said locking lever for holding said guard in a retraction or reception position with respect to said needle.

5. The assembly of claim 4 wherein said needle guard has a slot that extends from a distal to a proximal end and is engageable by said hub along said slot.

6. The assembly of claim 5 wherein said hub has a neck of reduced cross section and said slot has a non-uniform width to accommodate said neck when said guard is in position to cover said needle.

7. The assembly of claim 6 wherein said neck includes an extension above the engagement of said neck with said needle guard.

8. The assembly of claim 7 wherein said hub includes a channel for said catheter and said extension receives a tube that communicates with said channel;
    thereby to permit fluid to be injected or withdrawn through said tube.

9. The assembly of claim 8 wherein said tube has an input port connected to Luer fitting.

10. The assembly of claim 9 wherein said Luer fitting includes a flow-control valve.

11. The assembly of claim 10 wherein said Luer fitting is connectable to a hydrophobic filter cap.

12. A method of administering a catheter to a patient comprising the steps of: grasping a catheter hub having a needle and catheter therein protected by a needle guard that is slidably mounted on a housing for said needle;
    retracting said needle guard and inserting said needle and said catheter into a patient;
    retracting said needle over said housing into said needle guard to withdraw it from said catheter and disengage said needle guard from said hub, with said needle completely shielded by said needle guard.

13. The method of claim 12 wherein the step of retracting said needle comprises:
    extending said needle into said needle guard until said needle and said needle guard are completely disengaged from said hub.

14. The method of claim 12 wherein said sliding of said needle guard is continued until a locking detent mechanism of said housing is engaged.

15. A method of inserting a catheter into a patient comprising the steps of:
    retracting a needle guard slidably mounted over a housing having a needle extending therefrom with a catheter disposed along the length of said needle;
    inserting said needle and said catheter into a patient and thereafter retracting said needle from said catheter while maintaining said catheter in said patient by manually retracting said needle into said needle guard; and disengaging said needle guard from said catheter with said needle completely enclosed in said guard to permit unit removal of said housing, said needle guard and said needle while said catheter remains in said patient.

16. A percutaneously insertable over-the-needle catheter assembly (10), comprising:

a tubular catheter (31) having a proximal end, a distal end, and a tubular lumen extending axially therethrough;

a needle (51) having a proximal end and a sharpened distal end axially disposed within the lumen of said tubular catheter with the sharpened distal end of the needle extending beyond the distal end of said tubular catheter;

a needle guard (60) having an interior needle receiving passage and being axially retractable from a first needle position, where the sharpened distal tip of said needle is shielded by said needle guard, to a second needle position where said needle is exposed for insertion into a patient;

a plunger (53) attached to said needle for manually returning said needle to said first needle position where the sharpened distal end of said needle is completely shielded by said needle guard and disengaging said needle and needle guard from said catheter.

17. The catheter assembly of claim 16 further comprising a finger engagement tab attached to and extending outwardly from said plunger.

18. The catheter assembly of claim 16 wherein said plunger includes a channel in communication with the proximal end of said needle for providing controlled blood flashback to indicate that said catheter has been properly inserted into said patient.

19. A percutaneously insertable over-the-needle catheter assembly (10), comprising:

a tubular catheter (31) having a proximal end, a distal end, and a tubular lumen extending axially therethrough;

a needle (51) having a proximal end and a sharpened distal end axially disposed within the lumen of said tubular catheter with the sharpened distal end of the needle extending beyond the distal end of said tubular catheter;

a needle guard (60) having an interior needle receiving passage and being axially retractable from a first needle position, where the sharpened distal tip of said needle is shielded by said needle guard, to a second needle position where said needle is exposed for insertion into a patient;

a plunger (53) attached to said needle for manually returning said needle to said first needle position where the sharpened distal end of said needle is shielded by said needle guard and disengaging said needle and needle guard from said catheter;

wherein the said plunger and said needle guard further comprise:

a first detent lock portion (65a) formed on the needle guard; and a second detent lock portion (65b) formed on the needle guard;

said first and second detente lock portions being positioned and configured to engage a locking lever (56) of said plunger when said needle reaches said first or second needle position, thereby locking said needle in said first or second needle position.

* * * * *